US00PP25580P3

(12) United States Plant Patent
Talmadge

(10) Patent No.: US PP25,580 P3
(45) Date of Patent: May 26, 2015

(54) ***IPOMOEA* PLANT NAMED 'ISGBU07-0'**

(50) Latin Name: *Ipomoea batatas*
Varietal Denomination: ISGBU07-0

(71) Applicant: Paul A. Talmadge, Orcutt, CA (US)

(72) Inventor: Paul A. Talmadge, Orcutt, CA (US)

( * ) Notice: Subject to any disclaimer, the term of this patent is extended or adjusted under 35 U.S.C. 154(b) by 140 days.

(21) Appl. No.: 13/815,808

(22) Filed: Mar. 14, 2013

(65) Prior Publication Data

US 2014/0283254 P1 Sep. 18, 2014

(51) Int. Cl.
*A01H 5/12* (2006.01)
*A01H 5/00* (2006.01)

(52) U.S. Cl.
CPC ..... *A01H 5/00* (2013.01)
USPC ..... Plt./258

(58) Field of Classification Search
CPC ..... A01H 5/02; A01H 5/00; A01H 5/12; A01H 5/025; A01H 5/06
USPC ..... Plt./258, 226, 263.1, 373
See application file for complete search history.

(56) References Cited

U.S. PATENT DOCUMENTS

PP15,437 P3 * 12/2004 Pecota et al. ..... Plt./258

* cited by examiner

*Primary Examiner* — June Hwu
(74) *Attorney, Agent, or Firm* — Cassandra Bright

(57) ABSTRACT

A new and distinct *Ipomoea batatas* cultivar named 'ISGBU07-0' is disclosed, characterized by dark greyed-purple palmate shaped foliage with irregular green variegation. Plants are highly compact, have a bush forming, habit and produce many lateral branches, without pinching or chemical growth regulators. The new cultivar is an *Ipomoea batatas*, typically suited for ornamental container and garden use.

2 Drawing Sheets

Latin name of the genus and species: *Ipomoea batatas.*
Variety denomination: 'ISGBU07-0'.

BACKGROUND OF THE INVENTION

The new variety originated as a chance discover by the inventor, Paul A. Talmadge. The variety was discovered as a naturally occurring whole plant mutation from the patented variety *Ipomoea batatas* 'IPOSGDEEPUR'. The new variety was discovered in March of 2012 at a commercial greenhouse in Hudsonville, Mich.

After selecting and isolating the new cultivar, asexual reproduction of the new cultivar 'ISGBU07-0' was first performed by vegetative tip cuttings in a commercial greenhouse in Hudsonville, Mich. during 2012. 'ISGBU07-0' has since produced several generations and has shown that the unique features of this cultivar are stable and reproduced true to type. Typical asexual reproduction of the new variety is by vegetative cuttings.

SUMMARY OF THE INVENTION

The cultivar 'ISGBU07-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGBU07-0'. These characteristics in combination distinguish 'ISGBU07-0' as a new and distinct *Ipomoea* cultivar:

1. Bush forming plant habit
2. Unique foliage color of dark greyed purple with irregular green variegation.
3. Extremely compact plant habit.
4. Average to large foliage size.
5. Very well branched, without pinching or chemical growth regulator use.

PARENTAL COMPARISON

Plants of the new cultivar 'ISGBU07-0' are similar to the seed parent in most horticultural characteristics. However, 'ISGBU07-0' differs in producing foliage with green flecks. Additionally the new variety has a more compact plant habit.

COMMERCIAL COMPARISON

Plants of the new cultivar 'ISGBU07-0' can be compared to the commercial variety *Ipomoea batatas* 'Sweet Caroline Sweetheart Purple' U.S. Plant Pat. No. 18,573. Plants of 'ISGBU07-0' are similar to plants of 'Sweet Caroline Sweetheart Purple' in some horticultural characteristics, however, plants of 'ISGBU07-0' form a bush shape, with many short, secondary lateral branches, whereas 'Sweet Caroline Sweetheart Purple' will develop a vining, trailing habit with age, and requires pinching to develop lateral branches. Additionally plants of 'ISGBU07-0' are more compact and have foliage with irregular green variegation.

Plants of the new cultivar 'ISGBU07-0' can be compared to the commercial variety *Ipomoea batatas* 'Iposghpur' U.S. Plant Pat. No. 22,324. The new variety is similar to this comparator, however, the plant habit of 'ISGBU07-0' is more compact. Additionally, foliage of 'ISGBU07-0' has different shape, and contains green variegation not found on foliage of 'Iposghpur'.

BRIEF DESCRIPTION OF THE PHOTOGRAPHS

Figure 1:
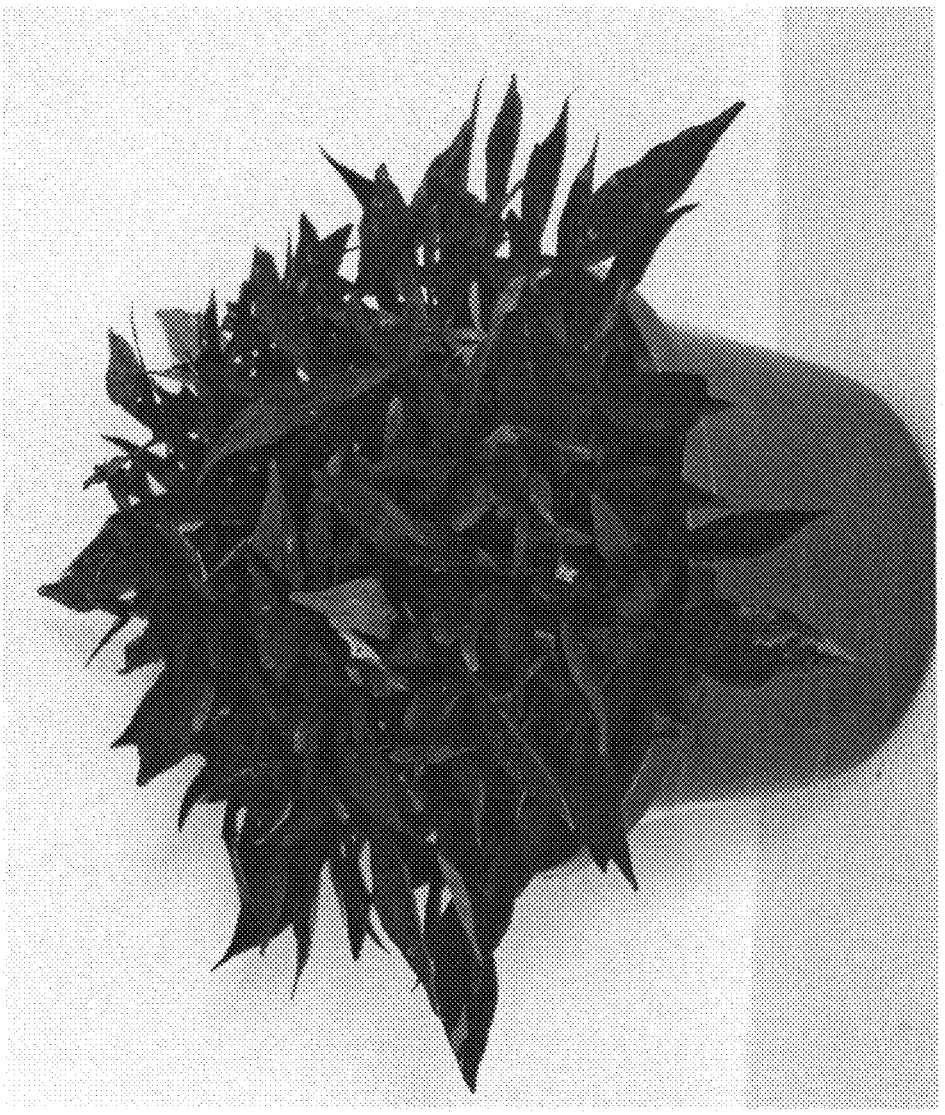

The accompanying photograph in FIG. 1 illustrates in full color a typical plant of 'ISGBU07-0' grown in a greenhouse in Oxnard, Calif. This plant is approximately 8 weeks old, from an unrooted cutting, shown in a 10 inch pot.

Figure 2:
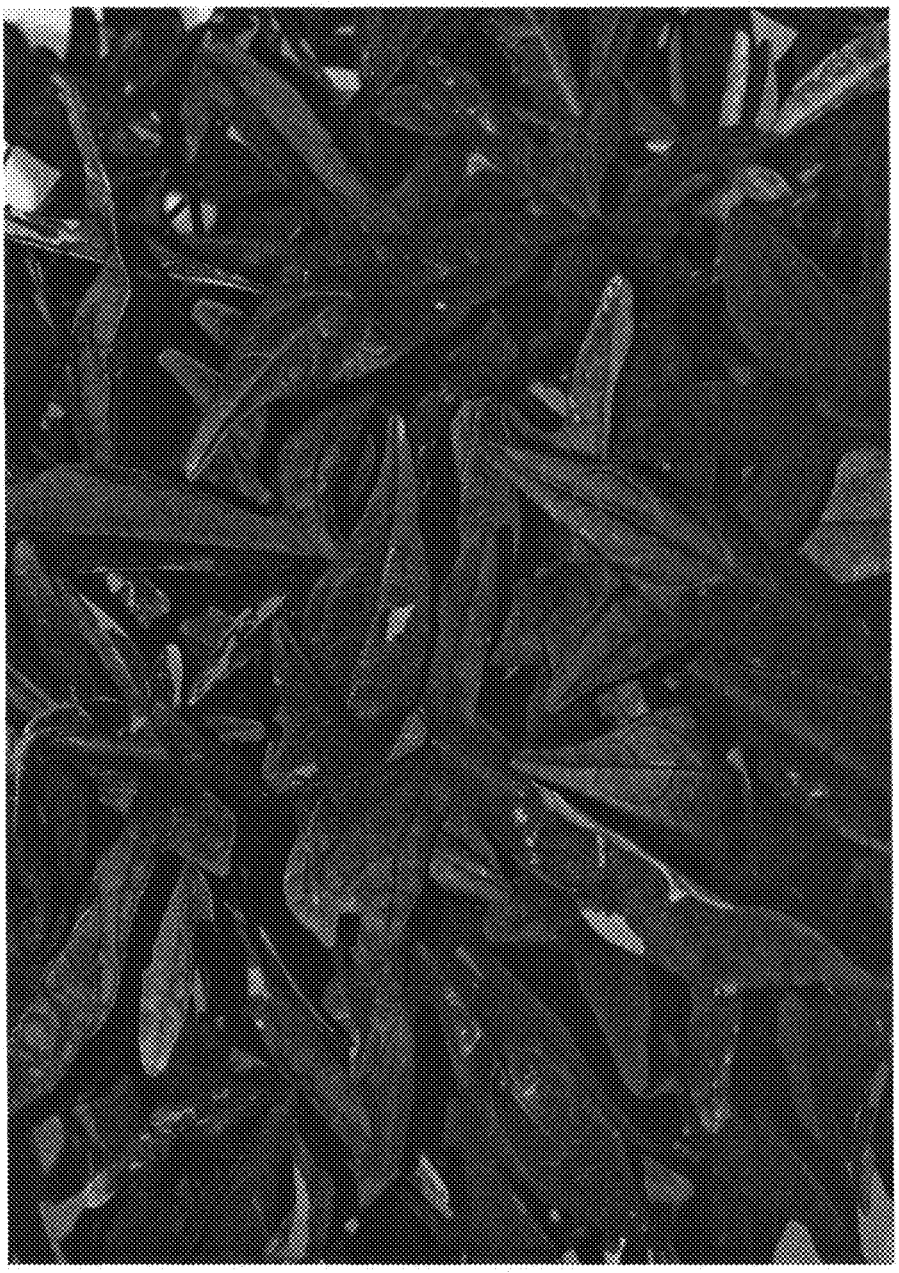

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGBU07-0' plants grown during the Spring months in a greenhouse in Oxnard, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGBU07-0'.

Age of the plant described: Approximately 8 weeks from an unrooted cutting.

Container size of the plant described: 10 inch commercial container.

PROPAGATION

*Propagation method*.—Terminal cuttings.

*Time to develop roots suitable for transplanting*.—Summer — about 6 days at an average temperature of 24° C.; Winter — about 10 days at an average temperature of 24° C.

*Root description*.—Thick, fleshy. Roots colored closest to RHS Yellow-White 158A.

*Tuber description*.—Irregular, oblong shape. Typically 1.5 to 4.5 cm in diameter and 2.5 to 6.0 cm long. Striated, eyes not present, colored near RHS Grey-Brown 199A, 199B and 199D. Flesh coloration near Greyed-Yellow 161D.

PLANT

*Growth habit*.—Compact, upright and mounding. Bushy.

*Height*.—Measured from top of soil line of pot, approximately 20 cm.

*Plant spread*.—Approximately 30 cm.

*Growth rate*.—Rapid.

*Branching characteristics*.—Very free branching, alternate or whorled occurring.

Primary lateral branches:

*Length*.—A range between 5 to 12 cm.

*Diameter*.—Approximately 0.6 cm.

*Texture*.—Glabrous, with occasional fine pubescence close to nodes.

*Color*.—Heavily flushed near RHS Greyed-Purple N186C over the main color of Yellow-Green 146D.

*Strength*.—Strong.

*Internode length*.—A range between 0.5-1.5 cm.

*Adventitious roots at nodes*.—Not observed.

Secondary lateral branches:

*Length*.—Ranging from 1 to 4 cm.

*Diameter*.—Approximately 0.4 cm.

*Texture*.—Glabrous, with occasional hairs seen with a hand lens.

*Color*.—Near Yellow-Green 146D, flushed near RHS Greyed-Purple N186C.

*Strength*.—Flexible.

*Internode length*.—Range between 0.4 to 0.6 cm.

*Quantity per 8 week old plant*.—Approximately 15.

*Adventitious roots at nodes*.—None observed.

New shoot growth characteristics:

*Color*.—Near Greyed-Purple 187B.

*Aspect*.—Upright.

*Texture*.—Glabrous.

FOLIAGE

Leaf:

*Arrangement*.—Alternate, simple.

*Average length*.—10 cm.

*Average width*.—8 cm.

*Shape of blade*.—Palmate with 2 very deep lobes and 2 deep lobes.

*Apex*.—Acute.

*Base*.—Cordate.

*Margin*.—Entire.

*Aspect*.—Upward fold and petiole attachment. Young foliage more folded.

*Texture of top surface*.—Glabrous.

*Texture of bottom surface*.—Glabrous.

*Quantity of leaves per lateral branch*.—Average 5 to 10.

FOLIAGE COLOR

*Young foliage upper side*.—Heavily mottled with Greyed-Purple N186B and Green 137B. Mottling completely irregular.

*Young foliage under side*.—Heavily mottled with Greyed-Purple N187A and Green 137C.

*Mature foliage upper side*.—Mainly near Greyed-Purple N186C, with blotches of Green 137A, Yellow-Green 144A and Greyed-Purple N186A. Blotching completely irregular.

*Mature foliage under side*.—Mainly near Greyed-Purple 187A, with blotches of Yellow-Green 144C.

VENATION

*Type*.—Palmate, reticulate.

*Venation color upper side*.—Near Greyed-Purple 187A.

*Venation color under side*.—Near Greyed-Purple N186C.

PETIOLE

*Length*.—A range from approximately 5 to 9 cm.

*Diameter*.—Approximately 0.4 cm at base, 0.25 cm at top.

*Texture*.—Mostly glabrous with a few hairs visible with a hand lens.

*Color*.—Near Greyed-Purple N186C, young foliage petioles Yellow-Green 144B flushed with Greyed-Purple N186C.

*Strength*.—Strong.

*Aspect*.—Straight to slightly curved.

FLOWER

Flowering: Not observed to date.

OTHER CHARACTERISTICS

Seeds and fruits: No seeds/fruits observed.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 40° C.

What is claimed is:

1. A new and distinct cultivar of *Ipomoea batatas* plant named 'ISGBU07-0' as herein illustrated and described.

* * * * *